United States Patent [19]

Kronenthal et al.

[11] Patent Number: 4,912,231

[45] Date of Patent: Mar. 27, 1990

[54] PROCESS FOR PREPARING (TRANS)-4-PHENYL-L-PROLINE DERIVATIVES

[75] Inventors: David Kronenthal, Yardley, Pa.; Paula L. Kuester, West Trenton; Richard H. Mueller, Ringoes, both of N.J.

[73] Assignee: E. R. Squibb & Sons, Inc., Princeton, N.J.

[21] Appl. No.: 209,165

[22] Filed: Jun. 17, 1988

Related U.S. Application Data

[63] Continuation-in-part of Ser. No. 61,511, Jun. 15, 1987, abandoned.

[51] Int. Cl.$^4$ ............................................. C07D 207/12
[52] U.S. Cl. ..................................... 548/533; 548/532
[58] Field of Search ............................... 548/532, 533

[56] References Cited

U.S. PATENT DOCUMENTS

4,501,901  2/1985  Thottathil et al. ................ 548/532
4,588,819  5/1986  Thottathil ........................ 548/532

OTHER PUBLICATIONS

Nakajima et al., Tetrahedron, vol. 25, pp. 1807–1816, 1969, "Stereospecific Alkylation of Benzene with (+)-Propylene Oxide by Lewis Acid Catalyst and Stereochemistry of Ring-Opening[1,2]".

Bauman et al., Journal of the American Chemical Society, 89:21, Oct. 11, 1967, pp. 5421–5424, "A Stereospecific Friedel–Crafts Reaction, The Alkylation of Benzene with γ-Valerolactone".

Green et al., J. Org. Chem. 1985, 50, 3945–3946, "Alkylation of Aromatic Compounds with Optically Active Lactic Acid Derivatives: Synthesis of Optically Pure 2-Arylpropionic Acid and Esters".

Nakajima et al., Bulletin of the Chemical Society of Japan, vol. 52 (8), 2377–2382 (1979), "Alkylation of Benzene with Optically Active 3-Chloro-1-butanol, 3-Chlorobutanoic Acid, and Their Esters".

Suga et al., Bull, Chem. Soc. Jpn., 54, 3611–3612 (1981), "Stereochemistry of Friedel–Crafts Alkylation of Benzene with Optically Active 2-Chlorobutane".

Streitwieser et al., J. Amer. Chem. Soc., 1965, 87, p. 4953, "Boron Fluoride-Alcohol Alkylations, III, Stereochemistry of Alkylation of Benzene with 2-Propanol-1-d$_3$[1]".

Hart, Friedel–Crafts and Related Reactions, ed. by G. A. Olah, vol. 1, pp. 999–1015, "Stereochemical Aspects".

Noller, Chemistry of Organic Compounds, 3rd Edition, 1965, p. 470.

Primary Examiner—Joseph Paul Brust
Attorney, Agent, or Firm—Burton Rodney

[57] ABSTRACT

A process is provided for preparing (trans)-4-phenyl-L-proline derivatives with excellent stereospecificity, which are useful in preparing certain ACE inhibitors, which process involves reacting a proline derivative of the structure

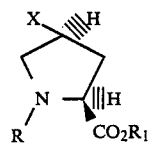

whereing R is a nitrogen protecting group, $R_1$ is H, aryl, arylalkyl or lower alkyl, and X is a leaving group such as fluorine, an alkyl sulfonate, arylsulfonate or cycloalkyl sulfonate is reacted with an aromatic nucleophile, such as benzene, in the presence of a Lewis acid such as AlCl$_3$ to form the (trans)-4-phenyl-L-proline derivative of the structure

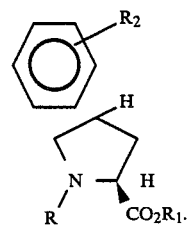

17 Claims, No Drawings

PROCESS FOR PREPARING (TRANS)-4-PHENYL-L-PROLINE DERIVATIVES

REFERENCE TO OTHER APPLICATIONS

This application is a continuation-in-part of application Ser. No. 61,511, filed June 15, 1987 now abandoned.

FIELD OF THE INVENTION

The present invention relates to a process for preparing trans-4-phenyl-L-proline derivatives with excellent stereospecificity, which derivatives are intermediates in the preparation of certain angiotensin-converting enzyme inhibitors.

DESCRIPTION OF THE INVENTION

In accordance with the present invention, a process is provided for preparing (trans)-4-phenyl-L-proline derivatives of the structure I

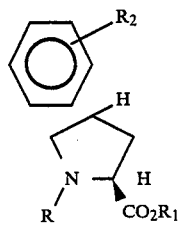

wherein R is a nitrogen protecting group (such as acetyl, benzoyl, p-anisoyl, p-nitrobenzoyl, trifluoroacetyl, o-toluoyl, p-toluoyl, p-tosyl, halobenzoyls such as p-chlorobenzoyl, o-chlorobenzoyl, p-bromobenzoyl, o-bromobenzoyl, p-iodobenzoyl, o-iodobenzoyl, and the like);

$R_1$ is H, aryl or lower alkyl, and $R_2$ is H, F, Cl or Br in the o or p positions or mixtures, which process includes the steps of reacting a proline derivative of the structure II

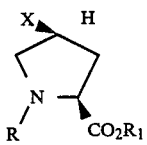

wherein R and $R_1$ are as defined above, and X is a leaving group (such as a halogen like F, Br or I, a $C_1$ to $C_6$ alkyl sulfonate like mesylate, isopropyl sulfonate, n-butyl sulfonate or triflate, an arylsulfonate like 2,4,6-triisopropyl benzene sulfonate or tosylate, or a cycloalkylsulfonate like cyclohexylsulfonate), with an aromatic nucleophile such as benzene, halosubstituted benzene (e.g., F-, Cl- or Br-substituted benzene) or phenyltrimethyl silane, in the presence of a Lewis acid and, if desired, recovering the trans-4-phenyl-L-proline derivative from the reaction mixture.

The process of the invention produces the desired (trans)-4-phenyl-L-proline I with excellent stereospecificity so that the ratio of trans:cis in the product I produced will be at least about 90:10, preferably at least about 95:5 and optimally at least about 98:2.

The reaction products obtained will include the trans-4-phenyl-L-proline derivative I as well as the side product III, for example where the leaving group X in II is mesylate or F.

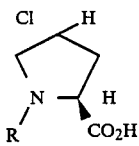

In addition, where X in proline derivative II is Cl or tosylate, then cis-4-phenyl-L-proline may be obtained as a by-product as well.

In carrying out the process of the invention, the proline derivative II will be employed in a molar ratio to the aromatic nucleophile of within the range of from about 1:5 to about 1:100 and preferably from about 1:10 to about 1:40, while the Lewis acid will be employed in a molar ratio to II of within the range of from about 2:1 to about 10:1 and preferably from about 3.6:1 to about 4.0:1. The reaction will be carried out at a reduced temperature of within the range of from about 5° to about 80° C. and preferably from about 7° to about 40° C., under an inert atmosphere such as argon or nitrogen, depending upon the proline derivatives II that is employed.

The starting derivative II when X is alkylsulfonate, such as mesyloxy may be prepared by treating lactone IV

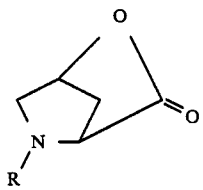

with methanol in the presence of an acid catalyst to afford hydroxy ester A

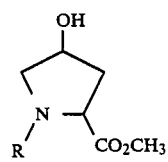

Treatment of A with an alkylsulfonyl chloride, arylsulfonyl chloride or cycloalkylsulfonyl chloride, such as methanesulfonyl chloride and a base such as triethylamine affords mesyl ester B

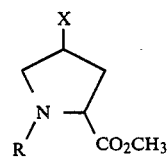

Treatment of B with lithium hydroxide affords II where $R_1$ is H.

The starting lactone IV may be prepared starting with the (trans)-4hydorxy-L-proline

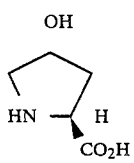

C which is treated with a protecting compound

RCl wherein "R" represents a nitrogen protecting group such as acetyl, benzoyl, p-anisoyl, p-nitrobenzoyl, trifluoroacetyl, o- or p-toluoyl, p-tosyl, p- or o-chlorobenzoyl or p- or o-bromobenzoyl to form the protected proline derivative E

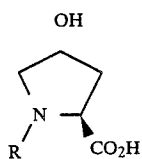

E

Proline E is then esterified with methanol in the presence of p-TsOH (that is p-toluenesulfonic acid monohydrate) and then the resulting ester is treated with p-TsCl and a base such as triethylamine or pyridine to form the tosylate F

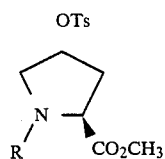

F which is treated with strong base such as sodium hydroxide to form the acid G

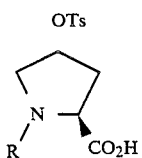

G

Acid G is then treated with weak base such as potassium carbonate in the presence of methylethyl ketone to form the lactone IV.

The starting proline derivative II wherein X is F may be prepared by treating a proline derivative of the structure

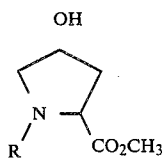

C' with diethylaminosulfur trifluoride and pyridine at a temperature within the range of from about −35° C. to about 25° C. employing a molar ratio of trifluoride:C' of within the range of from about 3:1 to about 1:1 in the presence of an inert organic solvent such as dichloromethane, to form the fluoro analog H

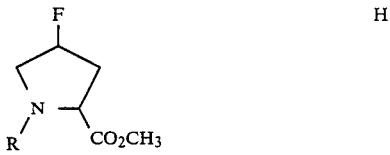

H which is subjected to a saponification reaction by treatment with lithium hydroxide to form proline II where X is F and $R_1$ is H.

Examples of starting lactone compounds IV and starting proline compounds II useful in carrying out the process of the invention include, but are not limited to, the following.

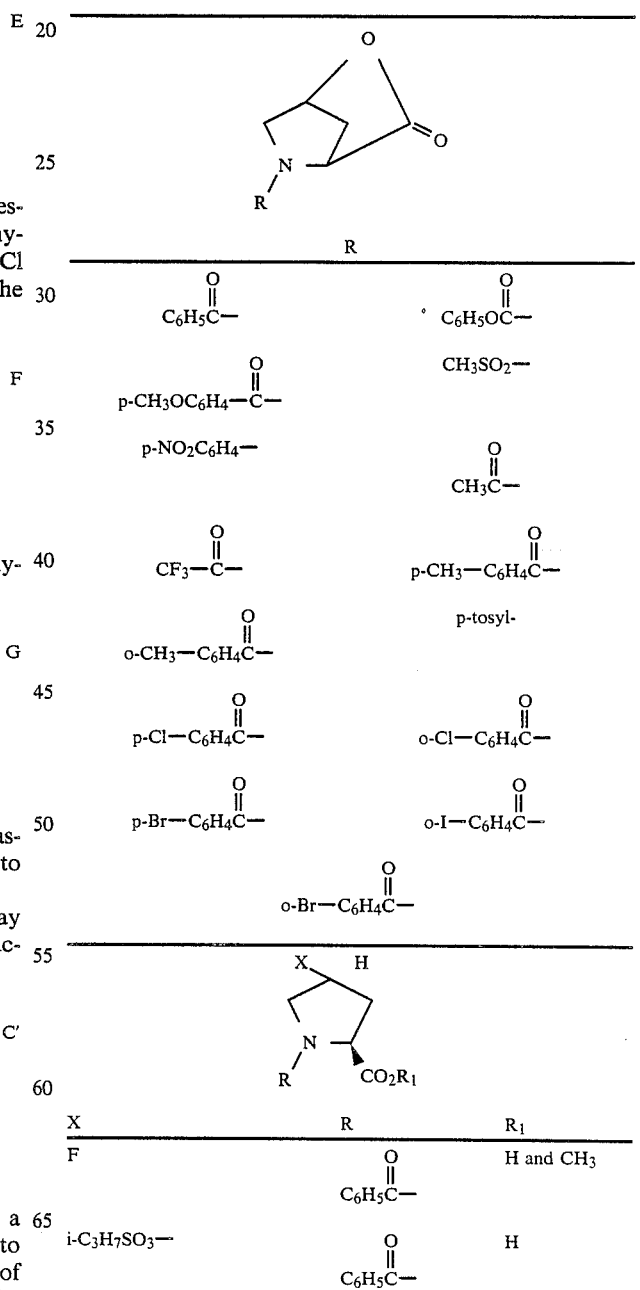

-continued

| | | |
|---|---|---|
| n-C4H9SO3— | C6H5OC(=O)— | H |
| Br | C6H5C(=O)— | C6H5— |
| mesylate | C6H5C(=O)— | C6H5— |
| triflate | CH3SO2— | H and CH3 |
| triflate | C6H5C(=O)— O— | CH3 and H |
| i-C3H7SO3— | p-NO2—C6H4— | C6H5— |
| Br | CH3C(=O)— | H |
| I | CF3—C(=O)— | H |
| mesylate | C6H5C(=O)— | H and CH3 |
| mesylate | p-Cl—C6H4C(=O)— | CH3 and H |
| cyclohexyl-SO3— | p-Br—C6H4C(=O)— | H and CH3 |
| (CH3)2CH—, (CH3)2CH—, CH3—CH(CH3)— substituted phenyl-SO3— | o-I—C6H4C(=O)— | H and CH3 |
| tosylate | C6H5C(=O) | H and CH3 |
| n-C4H9SO3— | p-tosyl | n-C3H7 |
| i-C3H7SO3— | o-Br—C6H4C(=O)— | H |
| F | o-Cl—C6H4C(=O)— | H and CH3 |

The trans-4-substituted-4-phenyl-L-proline derivatives I may be employed to form angiotensin converting enzyme inhibitors as described in U.S. Pat. No. 4,337,201 to Petrillo which covers fosinopril which has the following formula:

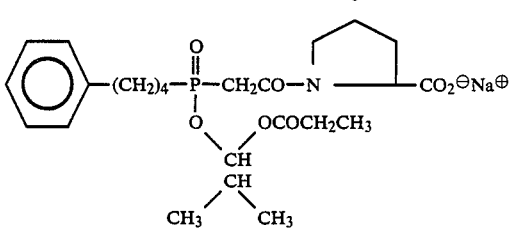

Listed below are definitions of the terms used in this specification. These definitions apply to the terms as they are used throughout the specification (unless they are otherwise limited in specific instances), either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to groups having 3 to 7 carbon atoms.

The term "aryl" refers to phenyl or phenyl substituted with halogen, alkyl, alkoxy, alkylthio, hydroxy, alkanoyl, nitro, amino, dialkylamino, or trifluoromethyl groups.

The term "alkanoyl" refers to groups having 2 to 9 carbon atoms.

The term "halogen" refers to fluorine, chlorine, bromine and iodine.

The following working Examples represent preferred embodiments of the present invention. Unless otherwise indicated, all temperatures are expressed in degrees Centigrade.

EXAMPLE 1

(trans)-1-Benzoyl-4-phenyl-L-proline

A. 1-Benzoyl-allo-hydroxy-L-proline lactone

A(1) (trans)-1-Benzoyl-4-hydroxy-L-proline

A 12-liter beaker equipped with an efficient shaft stirrer, a pH electrode and a 1-liter dropping funnel was installed in an ice bath. 4 Liters of water were charged to the beaker, and 1.31 kg (10.0 moles) of trans-4-hydroxy-L-proline was added with agitation to dissolve same. The dropping funnel was then charged with aqueous 10N sodium hydroxide solution. The pH of the mixture was raised to 8.0 with a little sodium hydroxide solution (about 25 ml). 300 ml of benzoyl chloride was then added and the agitation speed raised to assure efficient dispersion. Sodium hydroxide solution was added as required to maintain pH 8 and sufficient cooling was provided to maintain the mixture at about 25° C. As soon as most of the benzoyl chloride was consumed, another 300 ml portion of benzoyl chloride was added and the benzoylation continued. Two more 300 ml portions of benzoyl chloride were added in sequence. The benzoylation was allowed to come to completion at pH 8 and the mixture was stirred for an extra half hour while cooling to about 20° C.

A 4-liter separatory funnel was charged with 1 liter of isobutyl acetate. Part of the reaction mixture was added and equilibrated. The lower phase was allowed to settle and drain through a polish filter. More of the reaction mixture was added to the funnel until the total had been extracted. The IBA extract was discarded. The filtrate was returned to the 12-liter beaker and the dropping funnel was charged with concentrated hydrochloric acid. About 0.25 liters acid was added with efficient agitation to reach pH 4. Product seeds were added and agitation continued until a thin crystal slurry was formed and the pH did not climb anymore. Dropwise acid addition was resumed until the pH of the mixture was stable at 2.0. The total acid consumption was about 0.85 liters.

The crystal slurry was cooled to about 15° C. and agitated for an additional half hour.

The sandy crystals were collected on a Buchner filter with most of the mother liquor being removed by suction. Then the crystals were washed with cold water until the filtrate was free of chloride ions. Suction was continued until no more liquid emerged. The product was then dried to constant weight.

A(2) (trans)-1-Benzoyl-4-hydroxy-L-proline, methyl ester

A 5-liter flask was installed in an oil bath on a magnetic stirrer, provided with a reflux condenser and charged with 3.0 liters of methanol and 750 g (3.2 moles) of (trans)-1-benzoyl-4-hydroxy-L-proline. 19 grams of p-toluenesulfonic acid monohydrate (0.1 moles) were added. The mixture was heated to reflux and the esterification followed by TLC. Refluxing was continued until starting material was no longer detectable. 8 grams (0.1 moles) of sodium acetate was added to neutralize the catalyst acid. The condenser was set for distillation and the mixture concentrated at atmospheric pressure until the pot temperature reached 80° C. The distillate was then discarded. The clear residue was rapidly diluted with 2 liters of warm water. The flask was swirled for quick mixing and to permit the ester to crystallize. The slurry was cooled to room temperature with occasional swirling and maintained at room temperature for at least another hour. The crystals were collected on a filter and the filtrate recycled to aid in the transfer. The cake was pressed down and washed with one liter of cold water. The cake was sucked dry as possible and the product dried via a laboratory fluid bed dryer to constant weight. The combined filtrate was vacuum concentrated from the first crop to a small volume and the resulting slurry cooled to room temperature. A second crop of crystals was collected on a filter and washed with a minimum of cold water. The cake was pressed down and suction applied until no more liquid emerged. The second crop was dried to constant weight.

A(3) (trans)-1-Benzoyl-4-tosyloxy-L-proline methyl ester

540 Grams (2.84 moles) of technical p-toluenesulfonyl chloride were charged to a 5 liter flask. 1.5 Liters of anhydrous pyridine was added and the flask swirled to dissolve. Gradually, 600 g (2.40 moles) of (trans)-1-benzoyl-4-hydroxy-L-proline methyl ester were added and dissolved by swirling. The clear solution was maintained at room temperature and the conversion followed by TLC. After the starting material completely disappeared, the reaction mixture was transferred to a 12 liter beaker with an efficient agitator. 0.8 Liters of ice water and some tosylate seeds were added. Thick crystal slurry formed in about 10 minutes. Strong agitation was maintained and another 7 liters of an ice-water mixture were added over a period of one hour. The crystals were collected on a filter, the cake pressed down and washed with cold water until the effluent was free of chloride ions and suction applied to the cake until no more liquid emerged. The filtrate was discarded and the product dried to constant weight.

A(4) (trans)-1-Benzoyl-4-hydroxy-prolinetosylate

To a mixture of 6 liters of aqueous NaOH (81.6 g, 4.15 moles NaOH) and 1.6 liters of methanol were added Part A(3) tosylate (806.9 g, 2 moles) while holding the temperature between 25°-30° C. The mixture was stirred for 24 hours while holding the pH of the mixture between 11.0-11.5. The reaction mixture was filtered clear, the pH adjusted to 2.0 by addition of 37% aqueous hydrochloric acid (ca 175 ml) and stirring was continued for 1 hour at 20° C. The product was collected by filtration and the cake washed with water until Cl-test was nearly negative. Wet weight: 2400 g. The product was dried at 40° C. to a water content less than 5% by K.F.

| Yield: | 762.6 g | = 97.9% "as is" |
|---|---|---|
| | | = 93.4% corrected for $H_2O$ |

A(5) 1-Benzoyl-allo-hydroxy-L-prolinelactone

15 Liters of methyl ethyl ketone were added to a 50 liter reactor, followed by 731.6 g Part A(4) tosylate. 573.2 g $K_2CO_3$ were added with good agitation. The mixture was heated to reflux and held at reflux until TLC in-process control showed that reaction was complete. The reaction mixture was cooled to 15°-20° C. and the undissolved $K_2CO_3$ collected by filtration and washed with 15 liters of methyl ethyl ketone. The product rich filtrate was concentrated to about 1200-1300 g under reduced pressure. 2.3 Liters of n-hexane were added within 1 hour and the mixture stirred for 1 hour at 20° C. The precipitated title lactone was collected by filtration and washed with 700 ml of n-hexane. Wet weight: 532 g. The material was dried in vacuo to a constant weight of 332.7 g, 79.4%.

B. (cis)-1-Benzoyl-4-hydroxy-L-proline, methyl ester

A suspension of Part A lactone (100 g, 460.8 mmoles) in 2 liters of methanol was treated with p-toluenesulfonic acid monohydrate (1.28 g). The reaction was stirred 2 days at room temperature under argon. The methanol was removed in vacuo from the resulting solution. The residue was taken up in 1.4 liters of EtOAc, washed with saturated $NaHCO_3$ solution (3×300 ml), water (100 ml), and brine (100 ml), dried over $MgSO_4$, filtered, and concentrated in vacuo. The resulting white solid was recrystallized from EtOAc (100 ml), filtered, washed with cold EtOAc and dried in vacuo to yield 81.25 g (71%) of title compound.

M.P. 102.5°-104° C.

Anal Calcd for $C_{13}H_{15}NO_4$: C, 62.64; H, 6.07; N, 5.62. Found: C, 62.87; H, 6.03; N, 5.57.

C. (cis)-1-Benzoyl-4-[(4-methylsulfonyl)oxy]-L-proline

A solution of Part B proline derivative (80 g, 321.3 mmoles) in 1.6 liters of dichloromethane was treated with $Et_3N$ (67.17 ml, 482 mmoles). The solution was cooled to −15° C. in an acetone-dry ice bath and methanesulfonyl chloride (28.3 ml, 353 mmoles) was added via addition funnel. The reaction was very exothermic and care had to be taken to keep the temperature below −5°. After stirring for 30 minutes at −5° C. to −10° C., TLC (9:1 CH$_2$Cl$_2$:HOAc) indicated the reaction had gone to completion. The dichloromethane was removed in vacuo. The residue was taken up in ethyl acetate (1.5 liters), washed with 2×400 ml of water, 2×400 ml of 1 N HCl, 400 ml of saturated NaHCO$_3$ solution, 400 ml of brine, dried over MgSO$_4$, filtered, and concentrated in vacuo to a viscous oil. The oil was treated with 1 liter of THF (from a fresh bottle) and 200 ml of water. LiOH.H$_2$O (28.31 g, 674.7 mmoles) was added and the reaction was stirred for one hour. The THF was removed in vacuo and the pH was lowered to 1 with concentrated HCl. The aqueous mixture was extracted with 2×400 ml of ethyl acetate and the extracts were washed with 250 ml of water and then brine. At this point the extracts started to crystallize so they were transferred to an Erlenmeyer flask and recrystallized after boiling off 250 ml of ethyl acetate. The crystals were collected by filtration, washed with cold ethyl acetate and hexane, and dried in vacuo to yield 69.18 g of title compound as white prisms (69%).

M.P. 172°–173° C. (with decomposition).

Anal Calcd for C$_{13}$H$_{15}$NO$_6$S.0.05 H$_2$O: C, 49.69; H, 4.84; N, 4.46. Found: C, 49.48; H, 4.79; N, 4.42.

D. (trans)-1-Benzoyl-4-phenyl-L-proline

A dry, 3-necked 2l Morton flask (equipped with overhead stirrer, nitrogen inlet, and temperature probe) was charged with anhydrous aluminum chloride (124.23 g, 0.93 mole) followed by thiophene free benzene (810 ml). While stirring, the flask was cooled (dry ice-acetone) to an internal temperature of 6° C. Part C compound (powdered) was added (81 g, 0.26 mole) in portions. A rise in internal temperature to 7° C. was noted after the addition of ca. half the solid. The addition was briefly interrupted until the internal temperature returned to 6° C. and was then continued. The resulting heterogeneous mixture was vigorously stirred for 4 hours at 7°–8° C. and 1.5 hours at 8°–10° C. During this time the reaction became almost totally homogeneous and TLC indicated the conversion of Part C compound to a mixture of the title compound and (trans)-1-benzoyl-4-chloro- L-proline. The reaction was cooled to 7° C., and the mixture was hydrolyzed by the slow addition of 3N HCl (990 ml) such that the internal temperature did not rise above 30° C. The hydrolyzed mixture was treated with brine (180 ml), seeded with crystals of title compound, stirred at room temperature for 45 minutes and then held at room temperature overnight. The mixture was filtered through a coarse frit and the solid remaining in the reaction vessel was transferred to the funnel using 1N HCl (390 ml). The crude product was washed with water (4×500 ml). The last filtrate gave a weakly positive test for chloride (ethanolic silver nitrate). After drying on the filter for ca. 20 minutes the product weighed 122 g (159 mole %). The product was dried in vacuo to a weight of 98 g. The crude product was suspended in 240 ml of n-butyl acetate and heated to boiling. When the product dissolved, a second lower layer (presumably residual water) was evident. Boiling was continued until this layer disappeared. Sodium sulfate was added, boiling was continued an additional 5 minutes, and the mixture was filtered through celite (pre-washed with n-butyl acetate). The celite was washed with hot n-butyl acetate (2×ca. 50 ml). The filtrate volume was reduced to 240 ml, cooled, was seeded with crystals of title compound and stirred gently at ambient temperature overnight. The crystals were filtered and washed with n-butyl acetate (1×50 ml) and hexane (1×50 ml). The product was dried under high vacuum at 40° C. to a constant weight of 57.37 g (75.1 mole %; corrected for starting material and product HI). HPLC HI (λ218) of 99.03.

M.P. 137°–138.5° C.

[α]$_D$ = −62.3° (c=1.0, MeOH).

Anal Calcd for C$_{18}$H$_{17}$NO$_3$: C, 73.20; H, 5.80; N, 4.74. Found: C, 73.10; H, 5.81;, N, 4.72.

EXAMPLE 1A (trans)-1-Benzoyl-4-phenyl-L-proline

A suspension of aluminum trichloride (7.456 g, 55.91 mmole) in benzene (150 ml) was stirred under argon and treated with powdered (cis)-1-benzoyl-4-mesyloxy-L-proline (5 g, 15.93 mmole). The reaction was stirred at room temperature for 7 hours, cooled and treated slowly with 1N HCl (55 ml). After stirring 15 minutes, the mixture was transferred to a separatory funnel and treated with an additional 55 ml of 1N HCl followed by 20 ml of concentrated HCl and 250 ml of ethyl acetate. The layers were separated and the aqueous layer was washed with additional ethyl acetate (2×100 ml). The combined organic extracts were washed with water and brine and dried. Filtration and concentration in vacuo afforded 4.74 g of a white foam which was recrystallized from n-butyl acetate (seeding and sonication to initiate crystallization). The product was filtered, washed with n-butyl acetate and hexane, and dried in vacuo to 2.168 g of (trans)-1-benzoyl-4-phenyl-L-proline.

The mother liquor was evaporated and treated with DMF (50 ml) and potassium bicarbonate (868 mg). The resulting solution was stirred at 60°–65° C. under argon for 5 hours, treated with additional potassium bicarbonate (100 mg) and stirred an additional 2 hours. The DMF was mostly removed in vacuo at 35° C. and the residue was partitioned between ethyl acetate and water. The ethyl acetate layer (A) was washed twice with potassium bicarbonate solution. The combined aqueous extracts were acidified to pH 1.5 with HCl, extracted with ethyl acetate and washed with 1N HCl, water, brine and dried. Filtration and concentration in vacuo afforded 1.683 g (corrected for residual solvent) of (trans)-1-benzoyl-4-phenyl-L-proline. The overall yield for the experiment was (2.168 g +1.683 gm) 81%.

The ethyl acetate layer (A) from above was washed with brine, dried, filtered and concentrated in vacuo to 312 mg of 1-benzoyl-allo- hydroxy-L-proline lactone.

EXAMPLE 2

(trans)-1-Benzoyl-4-phenyl-L-proline

A. (cis)-1-Benzoyl-4-fluoro-L-proline methyl ester

A solution of (trans)-1-benzoyl-4-hydroxy-L-proline methyl ester prepared as described in Example 1 Part A(2) (6 g, 24.1 mmole) was dissolved in dichloromethane and cooled to −45° C. under an argon atmosphere. To the above solution diethylaminosulfur trifluoride (5.2 ml, 42 mmole) was added dropwise. The resulting solution was stirred and warmed to −35° C. To the above solution pyridine was added dropwise (9 ml, 116 mmole). The reaction was allowed to stir overnight while warming to room temperature. The solvent was removed in vacuo and the oily residue treated with ethyl acetate and 1N HCl. The mixture was transferred to a separatory funnel, the aqueous layer removed, and the organic layer washed with additional 1N HCl, then water and saturated sodium bicarbonate solution. The organic solution was dried over sodium sulfate, filtered and concentrated to a yellow oil. The crude product was chromatographed on silica gel using 1:1 ethyl acetate:hexane as eluent. Combination and concentration of product containing fractions produced 3.9 gm (64%) of title compound as an oil.

B. (cis)-1-Benzoyl-4-fluoro-L-proline

To a solution of Part A (cis)-1-benzoyl-4-fluoro-L-proline methyl ester (3.7 g, 14.74 mmole) in tetrahydrofuran-water (37 ml-7 ml) was added 31 ml of a 1N solution of lithium hydroxide in water. The reaction was stirred at room temperature for 2 hours. The tetrahydrofuran was evaporated, the pH of the residual aqueous solution was adjusted to 8 and extracted with ethyl acetate. The organic extracts were discarded. The aqueous phase was acidified to pH 2 with concentrated HCl and extracted with dichloromethane. The organic extracts were washed with brine and dried (sodium sulfate). The organic solution was filtered and concentrated to 2.9 g of solid.

The crude product was recrystallized by dissolving in ca. 100 ml of boiling ethyl acetate. The volume was reduced to ca. 75 ml, cooled and crystallization was allowed to proceed at room temperature overnight. The product was filtered, washed with ethyl acetate and hexane and dried in vacuo to 2.32 g (66%). M.P. 195°–197° C.

Anal Calcd for $C_{12}H_{12}NO_3F$: C, 60.76; H, 5.10; N, 5.91; F, 8.01. Found: C, 60.62; H, 5.09; N, 5.88; F. 8.23.

C. (trans)-1-Benzoyl-4-phenyl-L-proline

A suspension of aluminum trichloride (191 mg, 1.43 mmole) in benzene (5 ml) was stirred under argon and treated with Part B (cis)-N-benzoyl-4-fluoro-L-proline (100 mg, 0.42 mmole). The reaction was stirred at room temperature for 20 hours, cooled to 0° C. and hydrolyzed with 1N HCl. The layers were separated and the aqueous layer was extracted with ethyl acetate. The organic extracts were combined, washed with brine, dried and concentrated. The residue consisted of (a) (trans)-1-benzoyl-4-phenyl-L-proline (70%)
(b) (trans)-1-benzoyl-4-chloro-L-proline (30%).

The ratios were determined by spectrodensitometry at λ 260.

EXAMPLE 3

(trans)-1-Benzoyl-4-phenyl-L-proline (cis)-1-Benzoyl-4-mesyloxy-L-proline was subjected to the Friedel-Craft conditions outlined in Example 2C (reaction temperature=10° C., reaction time=5 hours) and worked up to afford a mixture as indicated below.

Product ratios were determined by HPLC at λ218.

| (a) | (trans)-1-benzoyl-4-phenyl-L—proline | 90.4% |
| (b) | (trans)-1-benzoyl-43-chloro-L—proline | 8.5% |
| (c) | (cis)-1-benzoyl-4-chloro-L—proline | 0.1% |
| (d) | (cis)-1-benzoyl-4-mesyloxy-L—proline | 0.2% |
| (e) | (trans)-1-benzoyl-4-mesyloxy-L—proline | 0.3% |

EXAMPLE 4

(trans)-1-o-Chlorobenzoyl-4-phenyl-L-proline

A. (cis)-1-o-Chlorobenzoyl-4-fluoro-L-proline

A solution of (cis)-4-fluoro-L-proline hydrobromide (Biochemistry, 4(11), 2507 (1965); 250 mg, 1.17 mmole) in 4 ml of water was prepared. The pH was adjusted to 7.8 with aqueous potassium carbonate. o-Chlorobenzoyl chloride (155 μl, 1.23 mmole) was added in three portions while maintaining the pH at 7.5-8.0. After the pH was stabilized, the reaction was transferred to a separatory funnel and washed with several portions of ethyl acetate. The aqueous layer was acidified to pH 2 with concentrated HCl, saturated with sodium chloride and extracted with ethyl acetate. The organic extracts were washed with brine, dried (sodium sulfate), filtered and concentrated to a solid. The crude product was recrystallized from ethyl acetate, filtered, washed with cold ethyl acetate and hexane and dried in vacuo to 204 mg (64%). M.P. 158°–160° C.

Anal Calcd for $C_{12}H_{11}ClFNO_3$: C, 53.05; H, 5.16; N, 5.16; Cl, 13.05, F, 6.99. Found: C, 53.25; H, 4.12; N, 5.17;, Cl, 12.86; F, 7.35.

B. (trans)-1-o-Chlorobenzoyl-4-phenyl-L-proline

A suspension of aluminum trichloride (100 mg, 0.75 mmole) in benzene (3.7 ml) was stirred under argon and treated with (cis)-1-o-chloro- benzoyl-4-fluoro-L-proline (60 mg, 0.22 mmole). After stirring overnight, the reaction was cooled, quenched with 1N HCl and extracted with ethyl acetate. The combined organic extracts were washed with brine, dried and concentrated in vacuo. The residue consisted of

| | Yields | |
| --- | --- | --- |
| | λ260 | NMR |
| (a) trans-1-o-chlorobenzoyl-4-phenyl-L—proline | 83% | 15% |
| (b) trans-1-o-chlorobenzoyl-4-chloror-L—proline | 17% | 15% |

Mass spectroscopy confirmed the presence of both products.

The stereochemistry of the products in this example was assumed to be trans based on the result for Example 2.

EXAMPLE 5

(trans)-1-o-bromobenzoyl-4-phenyl-L-proline

A. (cis)-4-Hydroxy-L-proline, methyl ester hydrochloride

Into a 1 liter Parr hydrogenation bottle was placed 29.90 g (107.12 mmol) of (cis)-1-benzyloxycarbonyl-4-hydroxy-L-proline, methyl ester (reference: J. Am. Chem. Soc., 79, 185, (1957)), 400 ml of methanol, 9.83 ml (117.90 mmol) of concentrated HCl, and 3.00 g of 10% palladium on activated carbon. The mixture was shaken under a hydrogen atmosphere at 50 psi for 4 hours, then filtered through a Millipore filter; the palladium was washed with 100 ml of methanol. The filtrate was concentrated under vacuum to a minimal volume, then treated with 250 ml of ethyl acetate, which caused a white precipitate to form. The solids were filtered, washed twice with ethyl acetate and once with hexane, and dried under vacuum to yield 20.05 g (93.1%) of the title compound.

MS: m/e 146 (M+H⊕, free amine).

Anal. (corrected for 1.07 equivalent H$_2$O as determined by Karl Fischer analysis): Calcd: C, 35.88; H, 7.09; N, 6.98; Cl, 17.65. Found: C, 36.09, H, 7.47; N, 6.86; Cl, 17.17.

m.p 100.9°–101.0° C.

B. (cis)-1-o-Bromobenzoyl-4-hydroxy-L-proline, methyl ester

Into a flame-dried 100 ml three-necked round-bottomed flask containing 30 ml of distilled THF was placed 3.00 g (16.575 mmol) of (cis)-4-hydroxy-L-proline, methyl ester; the vessel was immersed in an ice-/water bath and the suspension was allowed to stir under argon for 5 minutes. At this time, 6.35 ml (36.465 mmol) of diisopropylethylamine was added slowly via syringe; the mixture was allowed to stir for 10 minutes, whereupon 3.64 g (16.576 mmol) of 2-bromobenzoyl chloride was added dropwise via syringe over the course of 10 minutes. The mixture was allowed to stir at 0° for 2 hours then gradually brought to room temperature overnight. The mixture was concentrated under vacuum to a minimal volume, transferred to a separatory funnel, and diluted with 100 ml of ethyl acetate, then washed with 1N HCl (2×30 ml), saturated sodium bicarbonate (2×30 ml), and brine (30 ml). The organic solution was dried over sodium sulfate, filtered, and concentrated under vacuum. Recrystallization from hot ethyl acetate yielded 3.034 g (55.6%) of the title compound, m.p. 145.5°–146.8° C.; a second recrystallization of the mother liquor yielded 1.726 g to bring the net yield to 4.760 g (87.3%).

Anal Calcd: C, 47.43; H, 4.59; N, 4.26; Br, 24.27. Found: C, 47.79; H, 4.20; N, 4.24; Br, 24.49.

C. 1-o-Bromobenzoyl-4-mesyloxy-L-proline

Following the procedure outlined in Example 1C, (cis)-1-o-bromobenzoyl-4-hydroxy-L-proline methyl ester was converted to (cis)-1-o-bromo-benzoyl-4-mesyloxy-L-proline (foam). MS(CI): m/e 392 (M+H), 390 (M-H).

D. (trans)-1-o-Bromobenzoyl-4-phenyl-L-proline

Following the procedure of Example 4B, (cis)-1-o-bromobenzoyl-4-mesyloxy-L-proline was converted to a mixture of:

(a) (trans)-1-o-bromobenzoyl-4-phenyl-L-proline 87%

(b) (trans)-1-o-bromobenzoyl-4-chloro-L-proline 13%

The relative percentages were determined by tlc densitometry (λ260). Mass spectroscopy confirmed the presence of both products. The stereochemistry of the product was assumed to be trans based on the results in Examples 1 to 3.

EXAMPLE 6

(trans)-1-Benzoyl-4-phenyl-L-proline

A. (cis)-1-Benzoyl-4-tosyloxy-L-proline, methyl ester

A solution of (cis)-1-benzoyl-4-hydroxy-L-proline, methyl ester (1.9 g, 7.63 mmole) in pyridine (6 ml) was stirred under argon and treated with p-toluenesulfonyl chloride (1.75 g, 9.16 mmole). The reaction was stirred overnight, treated with additional p-toluenesulfonyl chloride (0.145 g, 0.76 mmole) and stirred for 24 hours. Ice water was added followed by ethyl acetate. The organic layer was washed with 1N HCl, brine, and dried. Filtration and concentration in vacuo afforded the title compound as a foam which was used without purification in the subsequent step.

B. (cis)-1-Benzoyl-4-tosyloxy-L-proline

A solution of (cis)-1-benzoyl-4-tosyloxy-L-proline, methyl ester (from the previous step) in THF.H$_2$O (25 ml–5 ml) was stirred under argon and treated with lithium hydroxide mono hydrate (672 mg, 16 mmole). The reaction was stirred for 3 hours, concentrated in vacuo, acidified to pH 1.5 with HCl, and extracted with ethyl acetate. The organic extracts were dried, filtered and concentrated in vacuo to a white solid which was recrystallized twice from ethyl acetate to afford the title compound.

Anal Calcd for C$_{19}$H$_{19}$NO$_6$S: C, 58.60; H, 4.92; N, 3.60. Found: C, 58.80; H, 5.02; N, 3.59.

C. (trans)-1-Benzoyl-4-phenyl-L-proline

To a dry flask was added aluminum trichloride (58 mg, 0.435 mmole) and benzene (3 ml). While stirring under argon, (cis)-1-benzoyl-4-tosyloxy-L-proline (50 mg, 0.128 mmole) was added. After further stirring overnight, the reaction was cooled to 0° C. and quenched with 1N HCl. The resulting mixture was extracted with ethyl acetate and the organic extracts were washed with brine, dried, and concentrated in vacuo. The residue consisted of:

| | | % (densitometry, λ260) |
|---|---|---|
| (a) | (trans)-1-Benzoyl-4-phenyl-L—proline | 66% |
| (b) | (trans)-1-Benzoyl-4-chloro-L—proline | 17% |
| (c) | (cis)-1-Benzoyl-4-phenyl-L—proline or | 17% |
| (d) | (cis)-1-Benzoyl-4-tosyloxy-L—proline | | or a mixture of (c) and (d) which was not separable by tlc.

EXAMPLE 7

(trans)-1-Benzoyl-4-phenyl-L-proline

A. (cis)-1-Benzoyl-4-hydroxy-L-proline

A solution of lactone from Example 1, part A(5) (10.05 gm, 46.31 mmole) in THF-H$_2$O (100 ml –18 ml) was treated slowly with 1M lithium hydroxide (60 ml). The reaction was stirred at room temperature under argon for 2 hours, concentrated and acidified to pH 6 with HCl. The solution was washed several times with ethyl acetate, acidified to pH 1 with HCl, saturated with sodium chloride and extracted with ethyl acetate. The extracts were washed with brine, dried over sodium sulfate, filtered and concentrated to an oil which was crystallized from dichloromethane-hexane to afford 7.7 gm (71%) of the title compound.

mp 133°–136° C.

B. (cis)-1-Benzoyl-4-hydroxy-L-proline, benzyl ester

A solution of (cis)-1-benzoyl-4-hydroxy-L-proline (7.074 gm, 30.1 mmole) in acetone was treated dropwise with 1,8-diazabicyclo[5.4.0]- undec-7-ene (5.4 ml, 36.1 mmole) while cooling with a water bath. After stirring under argon for 10 minutes, benzyl bromide (4.3 ml, 36.1 mmole) was added dropwise. After stirring for 3 hours at room temperature, an additional aliquot (0.25 ml) of benzyl bromide was added. The reaction was stirred overnight and the acetone removed in vacuo. The residue was partitioned between ethyl acetate and 1N HCl. The organic layer was washed with additional HCl, sodium bicarbonate solution, brine, and dried (sodium sulfate). Filtration, followed by concentration in vacuo afforded a solid which was recrystallized from ethyl acetate. The yield of the title compound was 8.77 gm (90%).

mp 123°–125° C.

C. (cis)-1-Benzoyl-4-[(isopropylsulfonyl)oxy]-L-proline

A solution of (cis)-1-benzoyl-4-hydroxy-L-proline, benzyl ester (500 mg, 1.54 mmole) and triethylamine (322 μl, 2.31 mmole) in dichloromethane (10 ml) was stirred under argon at −10° C. and treated dropwise with isopropylsulfonyl chloride (190 μl, 1.69 mmole). The reaction was warmed to 0° C. over 3 hours and treated with additional triethylamine (30 μl) and isopropylsulfonyl chloride (45 μl). The reaction was stirred at room temperature overnight and diluted with ethyl acetate and washed with 1M HCl, sodium bicarbonate solution, and brine and dried (sodium sulfate). Filtration followed by evaporation afforded an oil which was treated with THF. Evaporation was followed by redissolving the oily residue in 10% aqueous THF (8 ml). The resulting solution was treated with lithium hydroxide monohydrate (129 mg, 3.08 mmole) dissolved in 3 ml of water. The resulting mixture was stirred under argon at room temperature for 2 hours, concentrated in vacuo, and diluted with water. The pH was adjusted to 8 and the aqueous solution was washed with ethyl acetate. The aqueous layer was acidified to pH 2 with HCl and extracted with dichloromethane. The extracts were washed with brine, dried (sodium sulfate), filtered and concentrated. The crude product was recrystallized from methanol-ethyl acetate to afford 413 mg (78%) of the title compound.

mp 190°–192° C.

Anal Calcd for $C_{15}H_{19}NO_6S$: C, 52.77; H, 5.62; N, 4.10; S, 9.34. Found: C, 52.53; H, 5.58; N, 4.02; S, 9.44.

D. (trans)-1-Benzoyl-4-phenyl-L-proline

Following the procedure outlined in Example 3 (4 hours reaction time), (cis)-1-benzoyl-4-[(isopropylsulfonyl)oxy]-L-proline was converted to a mixture of

| (a) trans-1-benzoyl-4-phenyl-L—proline | 92% |
|---|---|
| (b) trans-1-benzoyl-4-chloro-L—porline | 8% |

The ratios were determined by TLC spectrodensitometry at λ260. No cis-1-benzoyl-4-phenyl-L-proline was detected (detection limit ca. 2%).

EXAMPLE 8

(trans)-1-o-Bromobenzoyl-4-phenyl-L-proline

A.
(cis)-1-o-Bromobenzoyl-4-[(isopropylsulfonyl)-oxy]-L-proline

Following the procedure outlined in Example 7C, (cis)-1-o-bromobenzoyl-4-hydroxy-L-proline methyl ester was converted to the title compound (53% yield), m.p. 138.8°–140.1° C.

Anal Calcd for $C_{15}H_{20}NO_6S$: C, 42.87; H, 4.32; N, 3.33; S, 7.63.

Found: C, 42.90; H, 4.28; N, 3.34; S, 7.50; Br, 18.75.

B. (trans)-1-o-Bromobenzoyl-4-phenyl-L-proline (cis)-1-o-Bromobenzoyl-4-[(isopropylsulfonyl)oxy]-L-proline was subjected to the Friedel-Crafts conditions outlined in Example 2C and worked up to afford a mixture consisting of:

(a)   (trans)-1-o-bromobenzoyl-4-phenyl-L-proline 95%

(b) (trans)-1-o-bromobenzoyl-4-chloro-L-proline 5%

The relative percentages were determined by tlc densitometry at λ260. Mass spectroscopy confirmed the presence of both products. The stereochemistry of the products was assumed to be trans based on the results in Examples 1 to 3.

EXAMPLE 9

(trans)-1-Benzoyl-4-phenyl-L-proline

A.
(cis)-1-Benzoyl-4-[(2,4,6-triisopropylbenzenesulfonyl)-oxy]-L-proline, benzyl ester A solution of (cis)-1-benzoyl-4-hydroxy-L-proline, benzyl ester (500 mg, 1.54 mmole) and pyridine (160 μl, 2.00 mmole) in dichloromethane (30 ml) was stirred under argon at room temperature and treated with 2,4,6-triisopropylbenzenesulfonyl chloride (512 mg, 1.69 mmole). The reaction was stirred at room temperature for 4 hours and treated with 4-dimethylaminopyridine (19 mg, 0.16 mmole), then stirred further for 1 hour. At this time, another portion of 4-dimethylaminopyridine (171 mg, 1.40 mmole) was added and the reaction stirred further for 16 hours. At this time, another portion of 2,4,6-triisopropylbenzenesulfonyl chloride (233 mg, 0.77 mmole) and of 4-dimethylaminopyridine (95 mg, 0.78 mmole) was added and the reaction allowed to stir further for 3 hours.

The reaction mixture was diluted with ethyl acetate (100 ml) and washed with 1N HCl (3×100 ml), saturated sodium bicarbonate (3×100 ml) and brine (100 ml). The organic solution was dried over sodium sulfate, filtered, and concentrated under vacuum to yield an oil.

This material was chromatographed on 60 g of silica gel (Merck, 230–400 mesh) using 3:1 hexane:ethyl acetate as eluent to yield an oil which solidified upon standing overnight, and yielded 692 mg (76%) of the title compound.

B. (cis)-1-Benzoyl-4-[(2,4,6-triisopropyl benzenesulfonyl)oxy]-L-proline

Following the procedure outlined in Example 2B, (4 equivalents LiOH, 6 hours), (cis)-1-benzoyl-4-[(2,4,6-triisopropylbenzenesulfonyl)oxy)-L-proline benzyl ester was converted to the title compound (56%).

Anal Calcd for $C_{27}H_{35}NO_6S$: C, 63.95; H, 7.08; N, 2.76; S, 6.32. Found: C, 63.92; H. 6.88; N, 2.62; S, 6.27.

C. (trans)-1-Benzoyl-4-phenyl-L-proline

Following the procedure outlined in Example 2C, (cis)-1-benzoyl-4-[2,4,6-triisopropylbenzenesulfonyl)oxy]-L-proline was converted to a mixture consisting of

| (a) (trans)-1-benzoyl-4-phenyl-L—proline | 71% |
|---|---|
| (b) (trans)-1-benzoyl-4-chloro-L—proline | 29% |

Product ratios were determined by tlc spectrodensitometry at λ260. Mass spectroscopy confirmed the presence of both products. No (cis)-1-benzoyl-4-phenyl-L-proline was detected by tlc (2% detection limit).

EXAMPLE 10

(trans)-1-Benzoyl-4-phenyl-L-proline

A. (cis)-1-Benzoyl-4-[(cyclohexylsulfonyl)oxy]-L-proline

A mixture of (cis)-1-benzoyl-4-hydroxy-L-proline benzyl ester (500 mg, 1.54 mmole) and triethylamine (0.36 ml, 2.58 mmole) in dichloromethane (10 ml) was stirred at −15° C. under argon and treated with a solution of cyclohexane sulfonyl chloride (422 mg, 2.31 mmole) in dichloromethane. The reaction was allowed to warm to room temperature while stirring overnight and treated with additional cyclohexanesulfonyl chloride (85 mg) and triethylamine (0.06 ml). After stirring an additional two hours, the solvent was evaporated and the residue partitioned between ethyl acetate and 1M HCl. The organic layer was washed with additional 1M HCl, sodium bicarbonate solution and brine. Drying followed by concentration under vacuum produced an oil (827 mg) which was dissolved in THF and hydrogenated over 10% Pd/C at 1 atm to produce the title compound (53%) after recrystallization from ethyl acetate.

MS (CI): 382 (M+H) 381 (M.−).

mp 154°–172° C. with decomposition.

B. (trans)-1-Benzoyl-4-phenyl-L-proline

Following the procedure outlined in Example 2C, (cis)-1-benzoyl-4-[(cyclohexylsulfonyl)oxy]-L-proline was treated with aluminum chloride and benzene to afford a mixture consisting of:

| (a) | (trans)-1-benzoyl-4-phenyl-L—proline | 87% |
| (b) | (trans)-1-benzoyl-4-chloro-L—proline | 13% |

EXAMPLE 11

(trans)-1-Benzoyl-4-phenyl-L-proline

A suspension of powdered (cis)-1-benzoyl-4-mesyloxy-L-proline (250 mg, 0.8 mmole) in 1,2-dichlorobenzene (3 ml) was stirred under argon and treated with phenyltrimethylsilane (1 ml, 5.8 mmole) followed by aluminum trichloride (383 mg, 2.87 mmole). The reaction was stirred overnight and an aliquot was removed, quenched into 1N HCl and extracted with ethyl acetate. Analysis of the organic layer by tlc showed the presence of:

| (a) | (trans)-1-benzoyl-4-phenyl-L—proline | 41% |
| (b) | (trans)-1-benzoyl-4-chloro-L—proline | 59% |

Yield by densitometry at λ260.

EXAMPLE 12

(cis)-1-Benzoyl-4-chlorophenyl-L-proline

A suspension of aluminum trichloride (364 mg, 2.72 mmole) in chlorobenzene (10 ml) was stirred at 0° C. under argon and treated with powdered (cis)-1-benzoyl-4-mesyloxy-L-proline. The reaction was stirred at 0° C. for 3 hours and room temperature overnight. The reaction was quenched at 0° C. by the addition of 1N HCl. The mixture was diluted with ethyl acetate. The organic layer was washed with sodium bicarbonate solution. The aqueous layer was acidified to pH 2 with HCl and extracted with ethyl acetate. The organic extracts were washed with brine, dried, filtered and concentrated in vacuo. Mass spectral analysis indicated the presence of (a) (trans)-1-benzoyl-4-chlorophenyl-L-proline and (b) (trans)-1-benzoyl-4-chloro-L-proline.

Spectrodensitometry of a tlc plate showed the ratio of a:b was 32:68 (λ260). The stereochemistry of the products in this example was assumed to be trans based on the result for Examples 1 to 3.

EXAMPLE 13

Alternative Preparation of (cis)-1-Benzoyl-4-mesyloxy-L-proline

A solution of (cis)-1-benzoyl-4-hydroxy-L-proline, methyl ester (169.2 g, 0.679 mole) and triethylamine (104.2 ml, 0.747 mole) in dichloromethane (3.3 liters) was cooled to −10° C. under nitrogen and treated dropwise with methanesulfonyl chloride (59.85 ml, 0.74 mole). The reaction was stirred an additional 30 minutes at −5° C. to −10° C. and the volatiles were removed in vacuo. The residue was treated with ethyl acetate and washed with water, 1N HCl, saturated sodium bicarbonate solution, and brine. The organic solution was dried, filtered, and concentrated in vacuo. The residue was dissolved in THF (2.1 liters) and treated with 3.36 N LiOH solution (423 ml) and stirred at room temperature for 1 hour. The THF was removed in vacuo and the aqueous solution was acidified to pH 4. The resulting solid was filtered, washed with ice water, and recrystallized from 95% ethanol-ethyl acetate to afford 130 g of the title compound.

EXAMPLES 14 TO 24

Following the procedure of Example 2(C) except substituting the (cis)-1-R-4-fluoro-L-proline shown in Column I below for the (cis)-1-benzoyl-4-fluoro-L-proline used in Example 2, the following products IIx and IIx were obtained.

| | Column I | Column II* | Column III* |
|---|---|---|---|
| | Ix | IIx | IIIx |

| | | TLC (λ260) | | |
|---|---|---|---|---|
| Ex. No. | R | IIx | IIIx | % of IIx (PMR) |
| 14. | p-anisoyl | 34 | 32 | and 2 demethylated products (15%, 19%). Required 4.4 equiv AlCl₃ |
| 15. | p-nitrobenzoyl | 40 | 46 | and 13.6% Ix. Used 5 equiv AlCl₃ |
| 16. | phenoxycarbonyl | 50 | 50 | |
| 17. | acetyl | | | 53 |
| 18. | trifluoroacetyl | | | 63 |
| 19. | o-toluoyl | 64 | 36 | |
| 20. | p-toluoyl | 65 | 35 | 62 |
| 21. | p-tosyl | 66 | 34 | 69 |
| 22. | benzoyl | 70 | 30 | |
| 23. | p-chlorobenzoyl | 74 | 26 | 73 |
| 24. | o-chlorobenzoyl | 83 | 17 | 84 |

*Trans stereochemistry confirmed for entry 22 by comparison with authentic samples.

For examples 16–17 and 20–24, mass spectroscopy confirmed the presence of IIX and IIIX.

What is claimed is:

1. A process for preparing (trans)-4-phenyl-L-proline derivatives with excellent stereospecificity, which comprises reacting a proline derivative of the structure

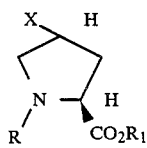

wherein

R is a nitrogen protecting group;

R₁ is H, aryl or lower alkyl; and

X is a leaving group, with an aromatic nucleophile in the presence of a Lewis acid as a catalyst, under an inert atmosphere, at a temperature of within the range of from about 5° to about 80° C., employing a molar ratio of proline derivative to aromatic nucleophile of within the range of from about 1:5 to about 1:100, and a molar ratio of Lewis acid to proline derivative of within the range of from about 2:1 to about 10:1, to form a reaction product containing the (trans)-4-phenyl-L-proline derivative of the structure

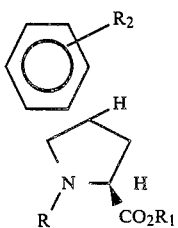

wherein R and R₁ are as defined above, and R₂ is H or halo, wherein the ratio of trans to cis in the reaction product is at least about 90:10, the term aryl as employed alone or as part of another group represents phenyl, or phenyl substituted with halogen, alkyl, alkoxy, alkylthio, hydroxy, alkanoyl, nitro, amino, dialkylamino or trifluoromethyl; and the aromatic nucleophile is benzene, halo-substituted benzene or phenyltrimethyl silane.

2. The process as defined in claim 1 including the step of recovering the (trans)-4-phenyl-L-proline derivative from the reaction mixture.

3. The process as defined in claim 1 wherein the aromatic nucleophile is halosubstituted benzene.

4. The process as defined in claim 1 wherein the aromatic nucleophile is benzene or phenyltrimethylsilane.

5. The process as defined in claim 1 wherein the proline derivative used as a reactant is employed in a molar ratio to the aromatic nucleophile of within the range of from about 1:10 to about 1:40.

6. The process as defined in claim 1 wherein the Lewis acid is aluminum chloride.

7. The process as defined in claim 1 wherein the nitrogen protecting group is benzoyl, mesyl, p-anisoyl, p-nitrobenzoyl, acetyl, trifluoroacetyl, o-toluoyl, p-toluoyl, p-tosyl, p-chlorobenzoyl, o-chlorobenzoyl, p-bromobenzoyl, o-bromobenzoyl, p-iodobenzoyl or o-iodobenzoyl.

8. The process as defined in claim 1 wherein the Lewis acid is employed in a molar ratio to the proline derivative reactant of within the range of from 2:1 to about 10:1.

9. The process as defined in claim 1 wherein the X leaving group is halogen, alkyl sulfonate, arylsulfonate or cycloalkylsulfonate.

10. The process as defined in claim 9 wherein X is fluoro, mesylate, triflate, tosylate, 2,4,6-triisopropylbenzene sulfonate, cyclohexyl sulfonate, isopropyl sulfonate or n-butyl sulfonate.

11. The process as defined in claim 1 wherein the proline derivative

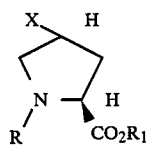

is reacted with benzene.

12. The process as defined in claim 11 wherein R is benzoyl, o-chlorobenzoyl or o-bromobenzoyl.

13. The process as defined in claim 12 wherein X is F, CH₃SO₂O— or i—C₃H₇SO₂O—.

14. The process as defined in claim 11 wherein X=F or mesyloxy, the reaction products include

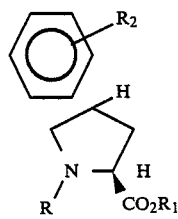

and

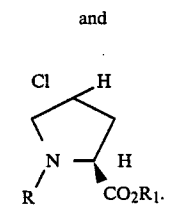

15. The process as defined in claim 1 wherein the proline derivative employed as a reactant has the structure and the Lewis acid is AlCl₃.

16. The process as defined in claim 1 wherein the reaction is carried out at a temperature within the range of from about 7° to about 40° C. C.

17. The process as defined in claim 1 wherein the reaction is carried out in the presence of an inert organic solvent under an inert atmosphere which is nitrogen or argon.

* * * * *